(12) United States Patent
Walsh

(10) Patent No.: US 11,628,025 B2
(45) Date of Patent: Apr. 18, 2023

(54) ROBOTIC SURGICAL SYSTEM FOR PROTECTING TISSUE SURROUNDING A SURGICAL SITE

(71) Applicant: INTEGRITY IMPLANTS INC., Palm Beach Gardens, FL (US)

(72) Inventor: Christopher Walsh, Palm Beach Gardens, FL (US)

(73) Assignee: INTEGRITY IMPLANTS, INC., Palm Beach Gardens, FL (US)

(*) Notice: Subject to any disclaimer, the term of this patent is extended or adjusted under 35 U.S.C. 154(b) by 0 days.

(21) Appl. No.: 17/671,369

(22) Filed: Feb. 14, 2022

(65) Prior Publication Data

US 2022/0211453 A1 Jul. 7, 2022

Related U.S. Application Data

(63) Continuation of application No. 16/258,517, filed on Jan. 25, 2019, now Pat. No. 11,259,882.

(60) Provisional application No. 62/622,112, filed on Jan. 25, 2018.

(51) Int. Cl.
*A61B 34/30* (2016.01)
*G16H 40/60* (2018.01)
*A61B 17/00* (2006.01)
*A61B 34/10* (2016.01)

(52) U.S. Cl.
CPC ............ *A61B 34/30* (2016.02); *G16H 40/60* (2018.01); *A61B 34/10* (2016.02); *A61B 2017/00261* (2013.01); *A61B 2034/303* (2016.02); *A61B 2562/0247* (2013.01)

(58) Field of Classification Search
CPC .......... A61B 2017/00261; A61B 17/56; A61B 34/10; A61B 34/30; A61B 2034/303; A61B 2562/0247; G16H 40/60
See application file for complete search history.

(56) References Cited

U.S. PATENT DOCUMENTS

| | | | |
|---|---|---|---|
| 6,933,695 B2 | 8/2005 | Blumenkranz | |
| 6,936,042 B2 | 8/2005 | Wallace et al. | |
| 6,994,703 B2 | 2/2006 | Wang et al. | |
| 6,994,708 B2 | 2/2006 | Manzo | |
| 7,027,892 B2 | 4/2006 | Wang et al. | |
| 7,048,745 B2 | 5/2006 | Tierney et al. | |
| 7,053,752 B2 | 5/2006 | Wang et al. | |
| 7,083,571 B2 | 8/2006 | Wang et al. | |
| 7,087,049 B2 | 8/2006 | Nowlin et al. | |
| 7,107,090 B2 | 9/2006 | Salisbury et al. | |
| 7,121,781 B2 | 10/2006 | Sanchez | |
| 7,125,403 B2 | 10/2006 | Julian et al. | |

(Continued)

*Primary Examiner* — Larry E Waggle, Jr.
(74) *Attorney, Agent, or Firm* — Brian S. Boyer; Syndicated Law, PC

(57) ABSTRACT

Systems and methods are provided for determining acceptable ranges of pressures for use by a robotic arm on a surgical instrument, robotic systems and methods that are limited to using the acceptable ranges of pressures, and the medical devices for use in the robotic surgery. Learning software is included in the methods and systems for correlating manually-performed procedures with pressure sensors as a tactile gauge for qualifying the acceptable ranges of pressures for use by a robotic system. Robotic systems and methods are provided for (i) locating tissue borders of a surgical site, (ii) identifying a preferred pressure, and (iii) transmitting the data to the computer to avoid violating the integrity of tissue surrounding the surgical site.

20 Claims, 7 Drawing Sheets

(56) References Cited

U.S. PATENT DOCUMENTS

| | | |
|---|---|---|
| 8,400,094 B2 | 3/2013 | Schena |
| 9,254,178 B2 | 2/2016 | Prisco et al. |
| 9,549,663 B2 | 1/2017 | Larkin |
| 11,259,882 B1 | 3/2022 | Walsh |
| 2012/0095458 A1 | 4/2012 | Cybulski et al. |
| 2018/0168754 A1 | 6/2018 | Overmyer |

ROBOTIC SURGICAL SYSTEM FOR PROTECTING TISSUE SURROUNDING A SURGICAL SITE

CROSS-REFERENCE TO RELATED APPLICATIONS

This is a continuation application of U.S. application Ser. No. 16/258,517, filed Jan. 25, 2019, which claims priority to U.S. Provisional Application No. 62/622,112, filed Jan. 25, 2018, each of which is hereby incorporated herein by reference in its entirety.

BACKGROUND

Field of the Invention

The present disclosure relates generally to robotic surgery, and more particularly to a system and related method for designing a robotic surgical procedure, for example, removal of spinal disc material and robotic endplate preparation during a spinal procedure.

Description of Related Art

One problem to address in establishing robotic surgical procedures is the pressure that the robotic arm applies on a surgical instrument in contact with tissue. One of skill will appreciate the value of having a method and system for qualifying an acceptable range of pressures applied to a functional portion of a surgical instrument against an animal tissue, for example, as well as the robotic systems and methods that can be derived from such a method.

By way of example only, the robotic vertebral endplate preparation system described herein includes a manual disc removal instrument, a robotic endplate preparation instrument, and a computer system. Optionally, the robotic vertebral endplate preparation system may further include a manual data input device, and/or a video display. The manual disc removal instrument is manually operable by a user (e.g. surgeon) to remove intervertebral disc material in a traditional manner (e.g. moved or rotated). The manual disc removal instrument is also equipped with one or more sensors to gather data related to the location of the annular borders and/or the preferred pressure for endplate preparation, and transmit the gathered data to the computer system in real-time (or alternatively store the data to be uploaded to the computer system upon completion of the data gathering). The computer system processes the annular border location and pressure data and to create a virtual model of the patient's annulus fibrosus to later inform the robotic endplate preparation instrument on the physical boundaries of the annulus as well as the preferred pressure to apply for precise and efficient preparation of the endplates. Optionally, the manual data input device (e.g. desktop computer, laptop computer, handheld tablet computer and/or smart-phone, and the like) may be used to manually input additional data points not obtained by the sensor. The video display (e.g. video monitor, desktop computer, laptop computer, tablet computer, and/or smart-phone) may show the real-time creation of the virtual model for instant visual feedback.

One of skill will appreciate having systems and methods for solving the above problems, and taking advantage of the opportunities available in the art of robotic surgical procedures including, for example, systems and methods that avoid violating the integrity of the tissue, such as tissue surrounding a surgical site that a surgeon wants to preserve. An example would be the vertebral endplate bone surrounding an intervertebral space. As such, one of skill will appreciate having (i) a system for qualifying an acceptable range of pressures applied to a functional portion of a surgical instrument against an animal tissue, and (ii) a method of qualifying a range of acceptable pressures for applying a functional portion of a surgical instrument against an animal tissue, as well as (iii) a robotic system calibrated to apply a range of acceptable pressures to an animal tissue through a functional portion of a surgical instrument.

SUMMARY

The technology provided herein includes, for example, systems and methods for determining acceptable ranges of pressures for use by a robotic arm on a surgical instrument, robotic systems and methods that are limited to using the acceptable ranges of pressures, and the medical devices for use in the robotic surgery. One of skill will appreciate, for example, that learning software is included in the methods and systems for correlating manually-performed procedures with pressure sensors as a tactile gauge for qualifying the acceptable ranges of pressures for use by a robotic system, at least in some embodiments.

A system for qualifying an acceptable range of pressures applied to a functional portion of a surgical instrument against an animal tissue can include, for example, a surgical instrument having a functional portion that contacts an animal tissue through application of pressure by an operator of the surgical instrument; and, a pressure sensor in an operable association with the functional portion operable to measure the pressure applied by the operator to the functional portion in contact with the tissue. One of skill will appreciate that the systems can also include a computer system having a processor; and, a memory. The memory can be configured to include, for example, a pressure module on a non-transitory computer readable storage medium operable to create pressure data representing the pressure applied by the operator to the functional portion in contact with the tissue; and, a database on a non-transitory computer readable storage medium operable to store the pressure data.

In some embodiments, the system can further include an input module on a non-transitory computer readable storage medium. The input module can, for example, receive input from an operator. The operator input can be used in identifying, for example, any surgical parameters of interest to a particular surgical procedure. For example, the operator input can include, the type of tissue receiving the pressure applied by the operator, the type of function obtained by the functional portion on the tissue receiving the pressure applied by the operator; or, the type of result, including a positive result and/or a negative result, of the pressure applied to the functional portion on the tissue receiving the pressure applied by the operator; or, a combination thereof of any of the parameters of interest.

In some embodiments, the system can further include a design module on a non-transitory computer readable storage medium operable for establishing a pressure output, or perhaps a pressure profile output corresponding to a range of acceptable pressures for use in contacting the type of tissue, to obtain the type of function, and the positive results, when contacting the functional portion with the tissue.

One of skill will appreciate that the systems and methods provided herein can be used to qualify the range of acceptable pressures for just about any type of surgical instrument that is used by applying a pressure to a tissue. For example, the surgical instrument can be a cutting instrument or a dissecting instrument, a grasping instrument or a holding instrument, a hemostatic instrument, a retraction instrument, or a tissue-unifying instrument.

The systems and methods can be used, in particular, to qualify the range of acceptable pressures for the functional portion of a spinal surgical instrument that is configured, for example, to remove intervertebral tissue. In some embodiments, for example, the surgical instrument can be configured for removal of nucleus pulposus, disc annulus, cartilaginous endplate, ligaments and fascia, or any combination thereof. In some embodiments, the surgical instrument is configured for removal of the intervertebral tissue without violating the integrity of the cortical portion of (i) the top vertebral plate or (ii) the bottom vertebral plate of an intervertebral space, wherein the removing includes limiting the pressure applied on the functional portion of the surgical instrument to the intervertebral tissue to a pressure from within the range of acceptable pressures.

One of skill will appreciate that the systems and methods can use any source of pressure to qualify the range of acceptable pressures. In some embodiments, the operator is a human, such that a human becomes a tactile gauge to help identify the range of acceptable pressures. In some embodiments, the operator is a mechanical device, such that a mechanical device becomes a tactile gauge to help identify the range of acceptable pressures. For example, a mechanical device can be any mechanical device used in in vivo, in vitro, or in situ procedures to apply and measure a mechanical pressure placed on a tissue. In some embodiments, for example, the mechanical device can be a robotic arm.

A method of qualifying a range of acceptable pressures is also provided for applying a functional portion of a surgical instrument against an animal tissue. The method can include, for example, obtaining a surgical instrument having a functional portion configured for contacting an animal tissue with a pressure applied by an operator of the surgical instrument, the functional portion of the surgical instrument being in an operable association with a pressure sensor for measuring the pressure applied by the operator to the functional portion in contact with the tissue; contacting the functional portion of the surgical instrument with the tissue of the animal with a total range of pressures; and, analyzing pressure data representing the total range of pressures. One of skill will appreciate that a computer can be used in some embodiments to analyze the data. The computer can have a processor and a memory, and the memory can have a pressure module on a non-transitory computer readable storage medium and a database on a non-transitory computer readable storage medium.

In some embodiments, the analyzing can include creating the pressure data with the pressure module, the pressure data representing the pressure applied by the operator to the functional portion in contact with the tissue; and, storing the pressure data on the database. The method steps can be designed, whether using a computer or otherwise, for use in the selecting a range of acceptable pressures for use in contacting the functional portion with the animal tissue.

The methods can further include correlating operator input with the results obtained from contacting the functional portion with the animal tissue, the correlating including, for example, receiving the operator input with an input module on a non-transitory computer readable storage medium; and identifying the type of tissue receiving the pressure applied by the operator, the type of function obtained by the functional portion on the tissue receiving the pressure applied by the operator, the type of result, including a positive result and/or a negative result, of the pressure applied through the functional portion on the animal tissue; or, a combination thereof.

The methods can further include designing a pressure profile using a design module on a non-transitory computer readable storage medium operable for establishing a pressure profile output that identifies a range of acceptable pressures for use in contacting the type of tissue, to obtain the type of function, and the positive results, when contacting the functional portion with the tissue.

A robotic system can be created, using the systems and methods herein, to apply a range of acceptable pressures to an animal tissue through a functional portion of a surgical instrument. Such a system can include, for example, a surgical instrument having a functional portion, a robotic arm configured for holding the surgical instrument and contacting the functional portion of the surgical instrument with an animal tissue using a pressure from within a range of acceptable pressures, a pressure application component operably coupled to the robot arm to apply the pressure from within the range of acceptable pressures when contacting the functional portion with the animal tissue. A computer can be included, and the computer can have a processor; and, a memory, wherein the memory can be configured to include, for example, a governing module on a non-transitory computer readable storage medium. The governing module can be configured such that it is operable to instruct the processor to limit any pressure applied by the robotic arm on the functional portion of the surgical instrument to fall within the range of acceptable pressures when contacting the functional portion with the animal tissue.

As with the qualifying methods and systems provided herein, one of skill will appreciate that the robotic systems and methods provided herein can implement the range of acceptable pressures with just about any type of surgical instrument that is used by applying a pressure to a tissue. For example, the surgical instrument can be a cutting instrument or a dissecting instrument, a grasping instrument or a holding instrument, a hemostatic instrument, a retraction instrument, or a tissue-unifying instrument.

The tissue of interest in the surgical procedure can include intervertebral tissue and cortical portion of a vertebral endplate, in some embodiments, and the functional portion of the surgical instrument can be configured to remove the intervertebral tissue, and the acceptable range of pressures can be designed to remove the intervertebral tissue without violating the cortical portion of the vertebral endplate. As such, the pressures applied on surgical instruments contacting tissue can be limited, for example, to what has been qualified to an acceptable range of pressures, as well as precise. It should be appreciated, however, that the systems and methods provided herein can be considered customizable to achieve any desired result, whether or not designed to be limited to an acceptable range of pressures, in order to obtain a desired result for any particular surgical procedure. In some embodiments, for example, a system or method may be designed to exceed what is otherwise considered to be an acceptable range of pressures, as it may be desired to have the functional portion of the surgical instrument achieve what was otherwise an undesired result. In some embodiments, for example, it may be desired to violate the integrity of a tissue, such as a bone tissue, whereas the acceptable range of pressures was qualified to avoid such a result.

In particular, however, a method of using the robotic systems taught herein can be controlled to prepare an intervertebral disc for a spinal fusion procedure. The procedure can be controlled to avoid violating the integrity of the cortical portion of a vertebral endplate, for example. Such a method might include, for example, creating a point of entry into an intervertebral disc, the intervertebral disc having a nucleus pulposus surrounded by an annulus fibrosis; and, removing the intervertebral tissue from within the intervertebral space, the intervertebral space having a top vertebral plate and a bottom vertebral plate while preserving the annulus fibrosis and without violating the integrity of the cortical portion of (i) the top vertebral plate or (ii) the bottom vertebral plate, wherein the removing includes limiting the pressure applied by the robotic arm on the functional portion of the surgical instrument to the intervertebral tissue to a pressure from within the range of acceptable pressures.

In some embodiments, the method can be part of a spinal fusion procedure that uses a scaffolding to support fusion of an intervertebral disc space, such that the method can further include inserting a scaffolding through the point of entry into the intervertebral space; and, adding a grafting material to the intervertebral space for the fusion.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

DETAILED DESCRIPTION

Figure 1:
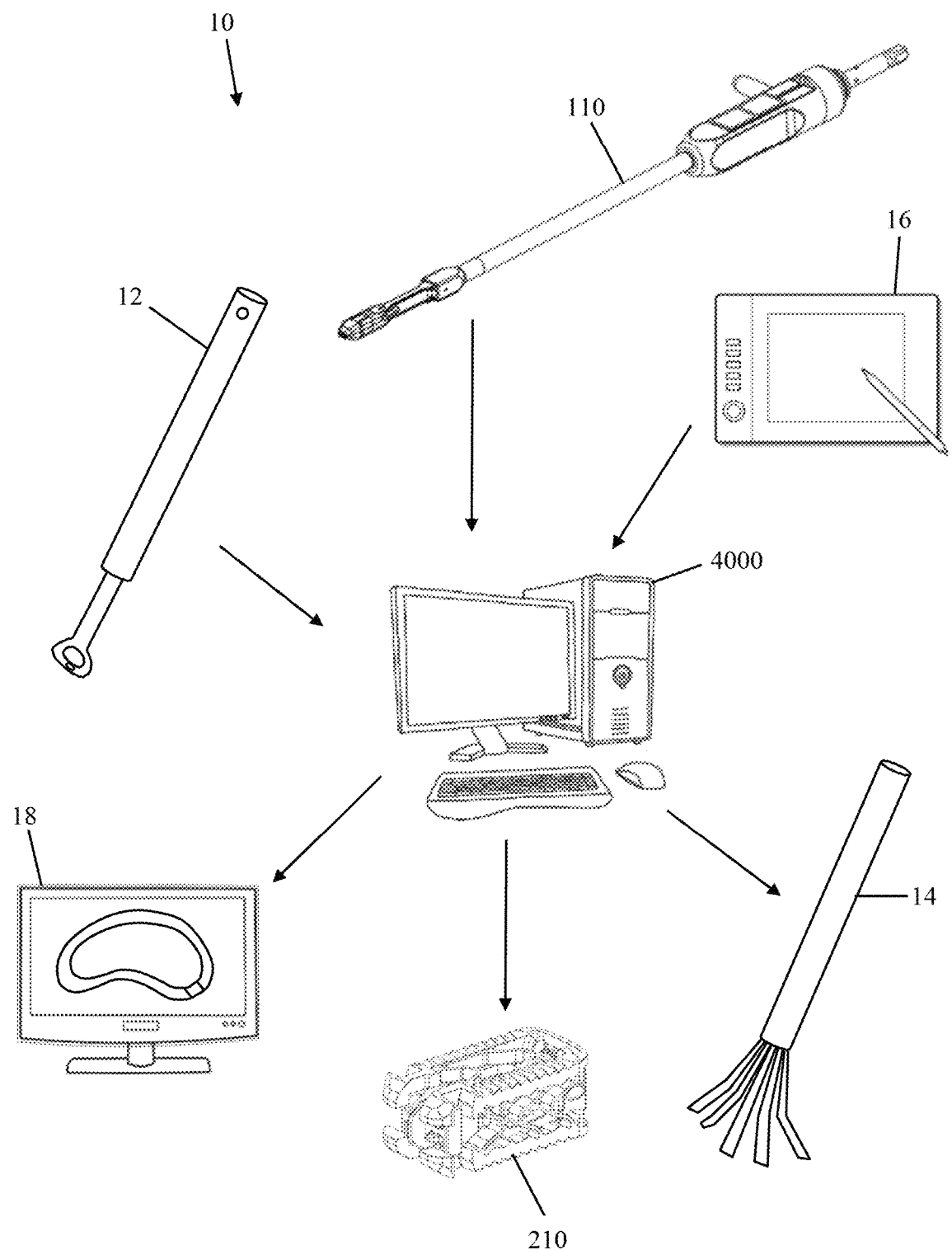
FIG. 1 is a graphical representation of an exemplary robotic vertebral endplate preparation system, according to some embodiments.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

Systems and methods are provided herein for determining acceptable ranges of pressures for use by a robotic arm on a surgical instrument, robotic systems and methods that are limited to using the acceptable ranges of pressures, and the medical devices for use in the robotic surgery. One of skill will appreciate, for example, that learning software is included in the methods and systems for correlating manually-performed procedures with pressure sensors as a tactile gauge for qualifying the acceptable ranges of pressures for use by a robotic system, at least in some embodiments. For purposes of this teaching, "qualifying" or "qualified" can include, for example, any experimental determination performed using the methods taught herein, which make it reasonable for a person of ordinary skill in the art of surgical procedures, and/or robotics, to believe that the results of applying the "acceptable" range of pressures would, for example, produce desirable results, in some embodiments, or would not result in a failure of the surgical procedure, in some embodiments.

A system for qualifying an acceptable range of pressures applied to a functional portion of a surgical instrument against an animal tissue can include, for example, a surgical instrument having a functional portion that contacts an animal tissue through application of pressure by an operator of the surgical instrument; and, a pressure sensor in an operable association with the functional portion operable to measure the pressure applied by the operator to the functional portion in contact with the tissue. One of skill will appreciate that the systems and methods can use any source of pressure to qualify the range of acceptable pressures. In some embodiments, the operator can be a human, such as a researcher, a medical doctor, or a surgeon, for example. The human can be used to help identify the range of acceptable pressures, as a tactile gauge and/or a source of tactile data. Tactile data can be used, for example, as a source of data to determine the range of acceptable pressures. In some embodiments, the operator can be a mechanical device, such that a mechanical device becomes a tactile gauge to help identify the range of acceptable pressures. For example, a mechanical device can be any mechanical device used in in vivo, in vitro, or in situ procedures to apply and measure a mechanical pressure placed on a tissue. In some embodiments, for example, the mechanical device can be a robotic arm as a tactile gauge, and/or a source of tactile data. In some embodiments, the operator can be a combination of a human and a mechanical device. For example, a human can operate a robotic arm, or other mechanical source of motion and pressure, and use the combination to provide a tactile gauge and a testimonial or measured response as a tactile gauge, and/or a source of tactile data, in some embodiments.

One of skill will appreciate that the systems can also include a computer system having a processor; and, a memory. The memory can be configured to include, for example, a pressure module on a non-transitory computer readable storage medium operable to create pressure data representing the pressure applied by the operator to the functional portion in contact with the tissue; and, a database on a non-transitory computer readable storage medium operable to store the pressure data.

One of skill will appreciate that the systems and methods provided herein can be used to qualify the range of acceptable pressures for just about any type of surgical instrument that is used by applying a pressure to a tissue. For example, the surgical instrument can be a cutting instrument or a dissecting instrument, a grasping instrument or a holding instrument, a hemostatic instrument, a retraction instrument, or a tissue-unifying instrument. Accordingly, one of skill will appreciate that the "functional portion" of the surgical instrument will include the portion of the surgical device that may be configured to do the "function", which can be, for example, the cutting or dissecting, the grasping or holding, the retracting, the tissue-unifying, the preventing of the flow of blood, or a combination thereof.

The term "animal" can be used interchangeably, in some embodiments, with the terms "subject" and "patient". Such terms can be used to refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like. As such, "tissue" can be used to refer, for example, to epithelial tissue, connective tissue, muscle tissue and/or nerve tissue, in some embodiments. One of skill will appreciate that epithelial tissues form the surface of the skin, and line many cavities of the body and covers the internal organs; connective tissue includes cartilage, bone, adipose, and blood, of which cartilage and bone are of particular focus herein; muscle tissue includes skeletal, smooth, and cardiac muscle; and the neural tissues include neurons that process and transfer information throughout a subject's body.

The tissue of interest in the surgical procedure can include, for example, intervertebral tissue and cortical portion of a vertebral endplate, in some embodiments. The functional portion of the surgical instrument can be configured, for example, to remove the intervertebral tissue. And, in some embodiments, the acceptable range of pressures can be designed to remove the intervertebral tissue without violating the cortical portion of the vertebral endplate. As such, the pressures applied on surgical instruments contacting tissue can be limited, for example, to what has been qualified to an acceptable range of pressures, as well as precise.

It should be appreciated, however, that the systems and methods provided herein can be considered customizable to achieve any desired result, whether or not designed to be limited to an acceptable range of pressures, in order to obtain a desired result for any particular surgical procedure. In some embodiments, for example, a system or method may be designed to exceed what is otherwise considered to be an acceptable range of pressures, as it may be desired to have the functional portion of the surgical instrument achieve what was otherwise an undesired result. In some embodiments, for example, it may be desired to violate the integrity of a tissue, such as a bone tissue, whereas the acceptable range of pressures was qualified to avoid such a result.

In particular, however, a method of using the robotic systems taught herein can be controlled to prepare an intervertebral disc for a spinal fusion procedure. The procedure can be controlled to avoid violating the integrity of the cortical portion of a vertebral endplate, for example. Such a method might include, for example, creating a point of entry into an intervertebral disc, the intervertebral disc having a nucleus pulposus surrounded by an annulus fibrosis; and, removing the intervertebral tissue from within the intervertebral space, the intervertebral space having a top vertebral plate and a bottom vertebral plate while preserving the annulus fibrosis and without violating the integrity of the cortical portion of (i) the top vertebral plate or (ii) the bottom vertebral plate, wherein the removing includes limiting the pressure applied by the robotic arm on the functional portion of the surgical instrument to the intervertebral tissue to a pressure from within the range of acceptable pressures.

In some embodiments, the method can be part of a spinal fusion procedure that uses a scaffolding to support fusion of an intervertebral disc space, such that the method can further include inserting a scaffolding through the point of entry into the intervertebral space; and, adding a grafting material to the intervertebral space for the fusion.

Moreover, one of skill will understand that the methods and systems provided herein can include hardware and software, in some embodiments, the combination of which can a "computer", for example, having a processor and memory. It should also be understood that the technology provided herein also includes "software", which can include instructions for execution of function by the processor, the software including, for example, a set of modules, engines, and instructions for executing the modules and/or engines by the processor. As such, in some embodiments, the system can further include an input module on a non-transitory computer readable storage medium. The input module can, for example, receive input from an "operator". The operator input can be used in identifying, for example, any surgical parameters of interest to a particular surgical procedure. For example, the operator input can include, the type of tissue receiving the pressure applied by the operator, the type of function obtained by the functional portion on the tissue receiving the pressure applied by the operator; or, the type of result, including a "positive result" and/or a "negative result", of the pressure applied to the functional portion on the tissue receiving the pressure applied by the operator; or, a combination thereof of any of the parameters of interest.

In some embodiments, the results can be expressed as "desirable". A "desirable result", in some embodiments, may be one that does not (i) represent a failure of the surgical procedure, or perhaps (ii) create an undue risk of future failure of the surgical procedure downstream for the subject undergoing the procedure, for example.

In some embodiments, the results can be expressed as a "positive". One of skill will understand that a "positive result" can be, for example, any surgical result obtained that is desired when contacting the functional portion of the surgical instrument with the tissue. A possible positive result may be the removal of connective tissue, such as fascia or cartilaginous tissue from the cortical portion of a bone without violating the cortical portion of the bone, or the integrity of the cortical portion of the bone, for example. In some embodiments, the tissue can be intervertebral tissue, for example, such as nucleus pulposus, disc annulus, cartilaginous endplate, ligaments and fascia, or any combination thereof, and the bone can be a vertebral endplate. In some embodiments, the tissue can be cartilaginous tissue, and the bone can be a tibial plateau or a femoral condyle. In some embodiments, the tissue can be cartilaginous tissue, and the bone can be a mandibular condyle, or a temporomandibular socket. A possible negative result could include for example, an attempt at the removal of the connective tissue from the cortical potion of the bone while, undesirably, violating the cortical portion of the bone. A "negative result" could be, for example, any undesirable result that was experience in the surgical procedure that was a result of an application of pressure through the functional portion of the surgical instrument when contacting the tissue with the functional portion.

In some embodiments, an "undesirable result" is anything less than a 100% positive result, 1% less than a 100% positive result, 2% less than a 100% positive result, 5% less than a 100% positive result, 10% less than a 100% positive result, 15% less than a 100% positive result, 25% less than a 100% positive result, 50% less than a 100% positive result, or any amount or range therein in increments of 0.1%. In some embodiments, a 100% positive result can be considered removal of a sufficient amount of connective tissue from a bone, for example, without removing any of the cortical portion of the bone.

The contrast is also used. For example, in some embodiments, an "desirable result" is anything less than a 100% negative result, 1% less than a 100% negative result, 2% less than a 100% negative result, 5% less than a 100% negative result, 10% less than a 100% negative result, 15% less than a 100% negative result, 25% less than a 100% negative result, 50% less than a 100% negative result, or any amount or range therein in increments of 0.1%. In some embodiments, a 100% negative result can be considered removal of a sufficient amount of a cortical portion of a bone to result in a failure of the surgical procedure.

As such, a "successful" a surgical procedure can be considered, in some embodiments, a lack of a significant loss of the integrity of a cortical portion of a bone, such that the structural integrity of the cortical portion of the bone at the surgical site remains sufficient for the surgical procedure to function as intended. However, a "failure" of a surgical procedure can be considered the point at which the integrity of the cortical portion of the bone was sufficiently lost, such that the cortical portion of the bone failed to support the local anatomical structure to the extent needed for the surgical procedure to function as intended. In a spinal fusion, for example, a failure can be considered the point at which the integrity of the cortical portion of the vertebral endplate failed to support to pressure applied to it by a cage, or a vertebral implant, or a scaffolding, in some embodiments. The percentage of a positive result, for example, can be measured relative to the total amount, or range of amounts, of a cortical portion of bone that one of ordinary skill would be expect to result in such a failure of the surgical procedure, if removed.

As such, the input module can be used to provide operator input in the form of, of example, tactile data that relates to such success or failure, or any such input, in order to better assess the range of acceptable pressures that can be applied through the functional portion of the surgical instrument in contact with the tissue. In some embodiments, the system can further include a design module on a non-transitory computer readable storage medium operable for establishing a pressure output, or perhaps a pressure profile output corresponding to a range of acceptable pressures for use in contacting the type of tissue, to obtain the type of function, and the positive results, when contacting the functional portion with the tissue. One of skill will appreciate that a pressure output can include a single pressure value, whereas a pressure profile output can include a set of pressures that provide information regarding the range of pressures used as a tactile gauge that can be correlated, for example, with the tactile data, or results obtained during, or ultimately, from the surgical procedure.

One of skill will appreciate that any suitable pressure sensor known to those of skill in the art can be used, the selection of which can be considered particular to the application in which the sensor is used, and the environment in which the sensor is placed. Examples of sensors include, but are not limited to, a blade sensor, a beam and force sensor, a hermetic strain gauge, a plunger sensor, a torque and power meter sensor, a strain gauge. One of skill will appreciate that transducers can be used, for example, to convert analog data into digital data, which can be useful in the integration of computer systems to the technology taught herein, in some embodiments.

As such, a method of qualifying a range of acceptable pressures is also provided for applying a functional portion of a surgical instrument against an animal tissue. The method can include, for example, obtaining a surgical instrument having a functional portion configured for contacting an animal tissue with a pressure applied by an operator of the surgical instrument, the functional portion of the surgical instrument being in an operable association with a pressure sensor for measuring the pressure applied by the operator to the functional portion in contact with the tissue; contacting the functional portion of the surgical instrument with the tissue of the animal with a total range of pressures; and, analyzing pressure data representing the total range of pressures. One of skill will appreciate that a computer can be used in some embodiments to analyze the data. The computer can have a processor and a memory, and the memory can have a pressure module on a non-transitory computer readable storage medium and a database on a non-transitory computer readable storage medium.

And, in some embodiments, the analyzing can include creating the pressure data with the pressure module, the pressure data representing the pressure applied by the operator to the functional portion in contact with the tissue; and, storing the pressure data on the database. The method steps can be designed, whether using a computer or otherwise, for use in the selecting a range of acceptable pressures for use in contacting the functional portion with the animal tissue.

The methods can further include correlating operator input with the results obtained from contacting the functional portion with the animal tissue, the correlating including, for example, receiving the operator input with an input module on a non-transitory computer readable storage medium; and identifying the type of tissue receiving the pressure applied by the operator, the type of function obtained by the functional portion on the tissue receiving the pressure applied by the operator, the type of result, including a positive result and/or a negative result, of the pressure applied through the functional portion on the animal tissue; or, a combination thereof.

The methods can further include designing a pressure profile using a design module on a non-transitory computer readable storage medium operable for establishing a pressure profile output that identifies a range of acceptable pressures for use in contacting the type of tissue, to obtain the type of function, and the positive results, when contacting the functional portion with the tissue.

As such, the systems and methods can be used, in some embodiments, to qualify the range of acceptable pressures for the functional portion of a spinal surgical instrument that is configured, for example, to remove intervertebral tissue. In some embodiments, for example, the surgical instrument can be configured for removal of nucleus pulposus, disc annulus, cartilaginous endplate, ligaments and fascia, or any combination thereof. In some embodiments, the surgical instrument is configured for removal of the intervertebral tissue without violating the integrity of the cortical portion of (i) the top vertebral plate or (ii) the bottom vertebral plate of an intervertebral space, wherein the removing includes limiting the pressure applied on the functional portion of the surgical instrument to the intervertebral tissue to a pressure from within the range of acceptable pressures.

FIG. 1 is a graphical representation of an exemplary robotic vertebral endplate preparation system 10 according to one embodiment of the disclosure. By way of example only, the robotic vertebral endplate preparation system 10 includes a manual disc removal instrument 12, a robotic endplate preparation instrument 14, and a computer system 4000. Optionally, the robotic vertebral endplate preparation system may further include a manual data input device 16, and/or a video display 18. As will be explained, the manual disc removal instrument 10 is manually operable by a user (e.g. surgeon) to remove intervertebral disc material in a traditional manner (e.g. moved or rotated). The manual disc removal instrument 10 is also equipped with one or more sensors to gather data related to the location of the annular borders and/or the preferred pressure for endplate preparation, and transmit the gathered data to the computer system 4000 in real-time (or alternatively store the data to be uploaded to the computer system 4000 upon completion of the data gathering). The computer system 4000 (FIG. 9) processes the annular border location and pressure data and to create a virtual model of the patient's annulus fibrosus to later inform the robotic endplate preparation instrument 14 on the physical boundaries of the annulus as well as the preferred pressure to apply for precise and efficient preparation of the endplates. Optionally, the manual data input device 16 (e.g. desktop computer, laptop computer, hand-held tablet computer and/or smart-phone, and the like) may be used to manually input additional data points not obtained by the sensor. The video display 18 (e.g. video monitor, desktop computer, laptop computer, tablet computer, and/or smart-phone) may show the real-time creation of the virtual model for instant visual feedback.

Figure 2:
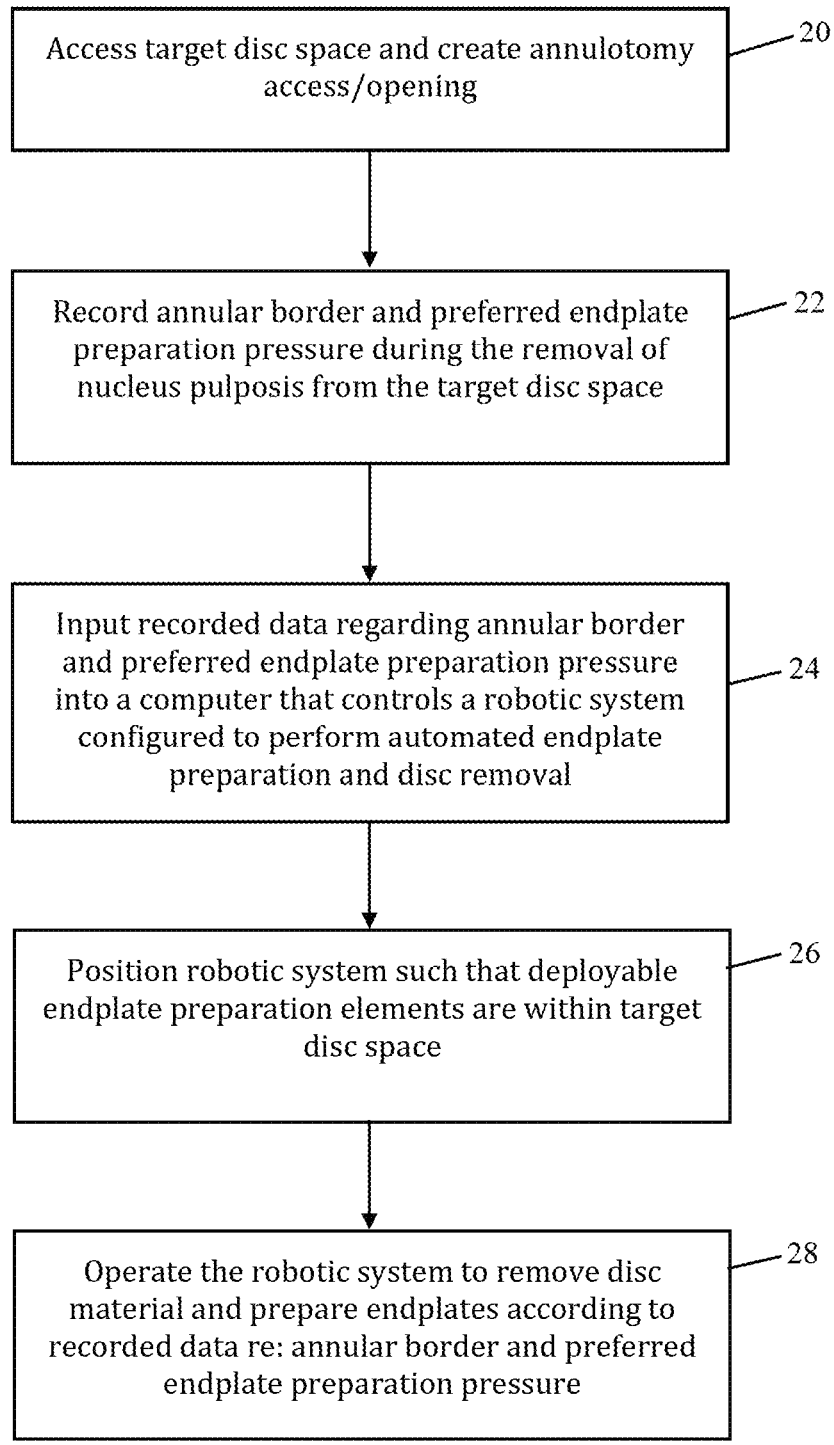
FIG. 2 is a flowchart illustrating one example of a method of performing robotic endplate preparation during a spinal procedure using the robotic vertebral endplate preparation system of FIG. 1, according to some embodiments.
Figure 3:
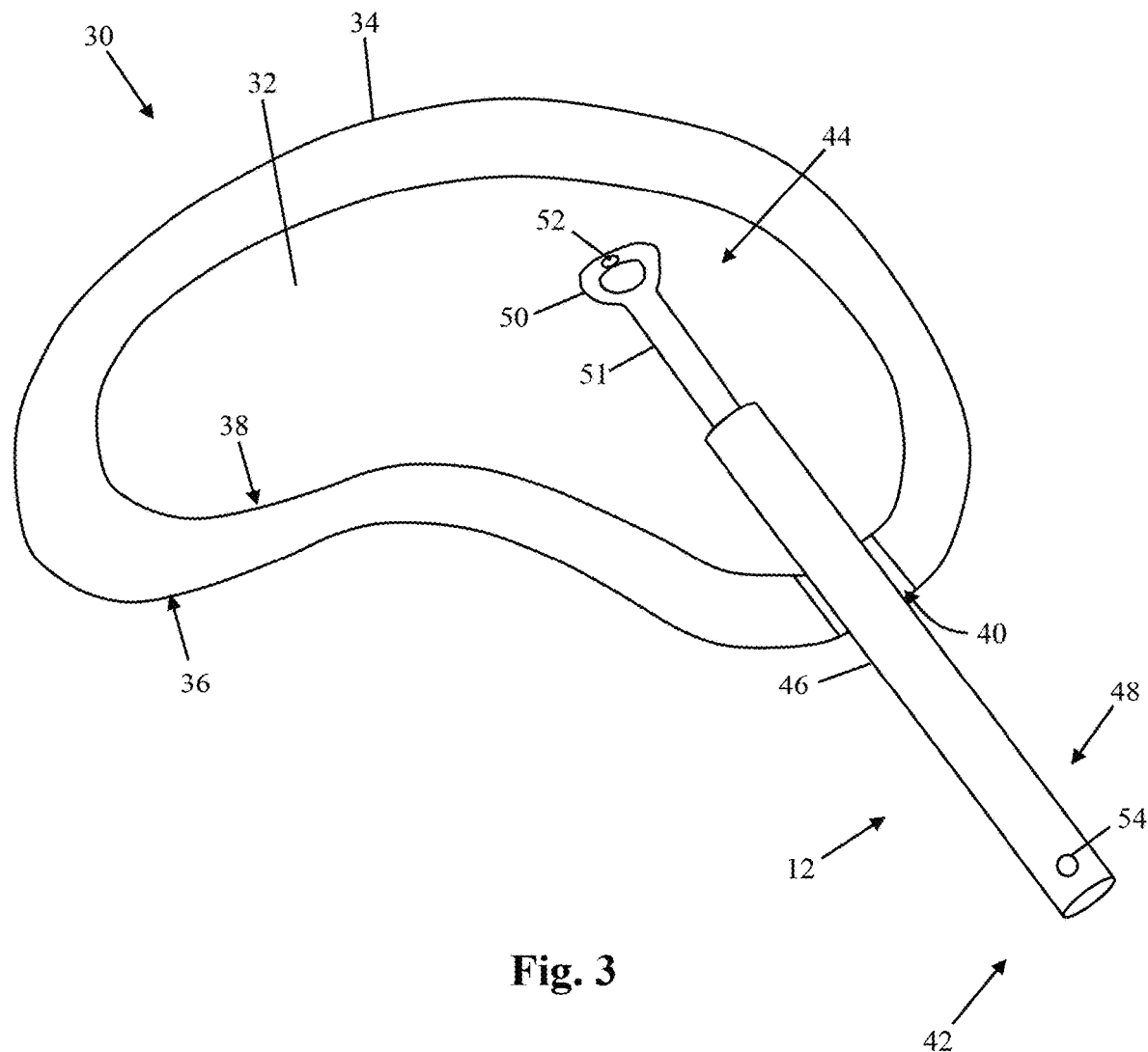
FIG. 3 is a perspective view of an example of the manual disc removal instrument of FIG. 1 in use within an intervertebral disc, according to some embodiments.
Figure 4:
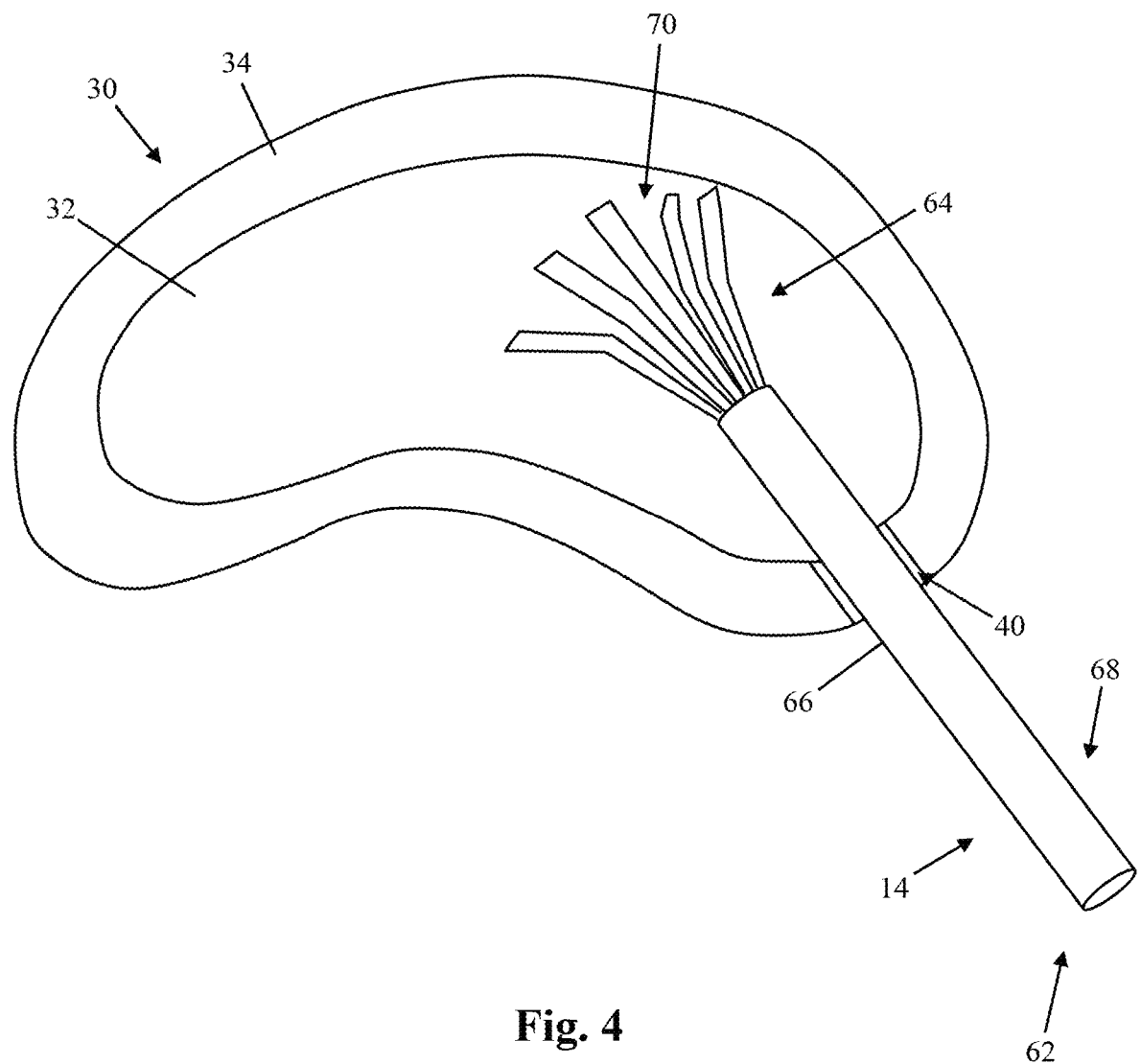
FIG. 4 is a perspective view of an example of the robotic endplate preparation instrument of FIG. 1 in use within an intervertebral disc, according to some embodiments.
Figure 5:
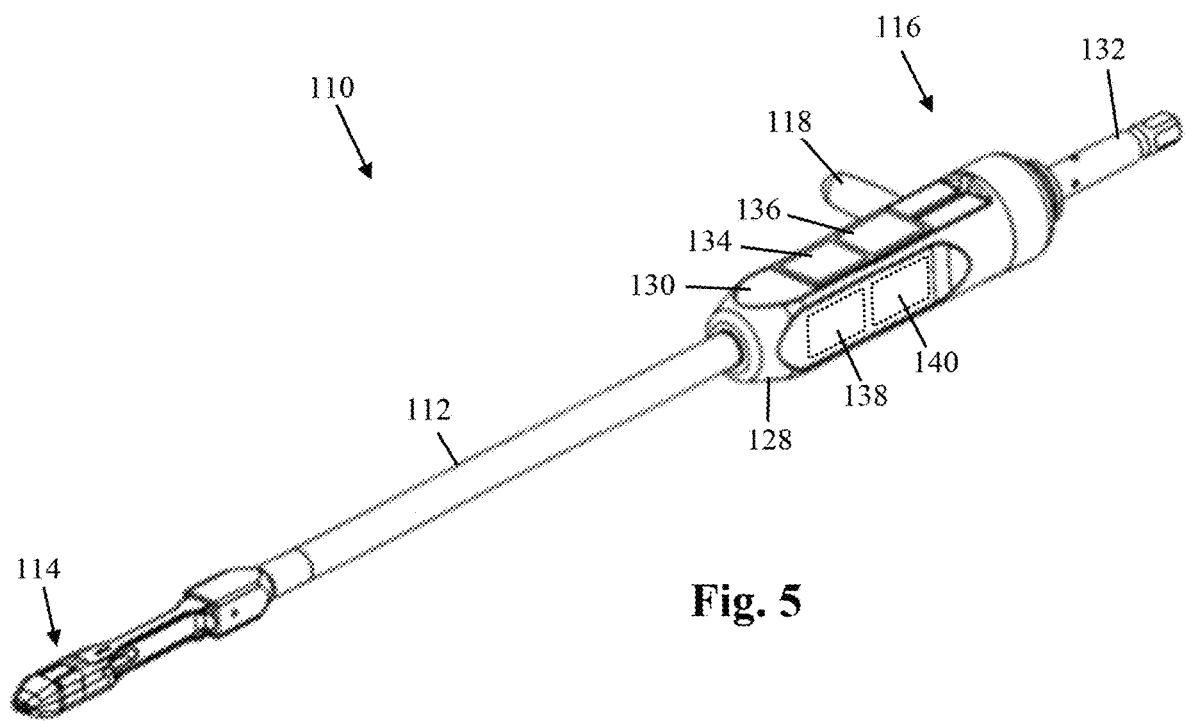
FIG. 5 is a perspective view of an example of a digital expandable trial instrument according to one embodiment of the disclosure, according to some embodiments.
Figure 6:
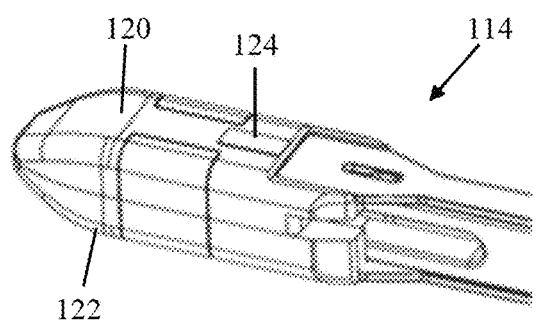
FIG. 6 is a top perspective view of the distal end of the digital expandable trial instrument of FIG. 5, according to some embodiments.
Figure 7:
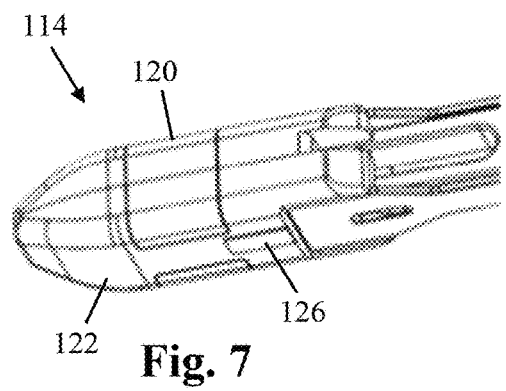
FIG. 7 is a bottom perspective view of the distal end of the digital expandable trial instrument of FIG. 6, according to some embodiments.

Referring to FIGS. 2-4, further description of the robotic vertebral endplate preparation system will proceed in conjunction with a description of the exemplary method for performing automated endplate preparation during a spinal surgery. FIG. 2 is a flowchart depicting the several steps of the example method. By way of example, the first step 20 is to access the target disc space and create annulotomy access/opening. By way of example, the method is described herein in the context of a minimally invasive approach to the target disc space through Kambin's Triangle, however target disc access may be accomplished in any traditional manner known in the field, including but not limited to open, percutaneous, and minimally invasive, as well as any desirable approach angle, including but not limited to anterior, posterior, posteriolateral, lateral, and Kambin's Triangle. Generally, once the target disc space has been identified and the approach angle determined (by any suitable method known in the art), an incision is made in the patient's skin and a surgical access corridor is established to the target disc space (e.g. using one or more cannulae, tissue retractors, and the like).

FIG. 3 illustrates an example of the manual disc removal instrument 12 (e.g. rasp) according to one embodiment of the disclosure in use within an intervertebral disc 30. The intervertebral disc 30 includes a nucleus pulopsus 32 ("nucleus") surrounded by an annulus fibrosus 34 ("annulus" or "annular wall"). The annulus 34 has a thickness dimension, and as such includes an outer boundary 36 and an inner boundary 38. Returning to the method description, once the access corridor is established, the nucleus 32 is accessed by creating a breach 40 in the annular wall 34. The user may then proceed to the next step 22, which is to manually remove some or all of the nucleus 32 using a disc removal instrument (e.g. the disc removal instrument 12 shown in FIG. 3), while at the same time mapping the annular border and determining the preferred endplate preparation pressure. The example manual disc removal instrument 12 of the present disclosure includes a proximal end 42, distal end 44, and an elongated shaft 46 extending between the proximal and distal ends. The proximal end 42 includes a handle 48 configured to enable manual manipulation of the instrument. The distal end 44 includes a shaped end 50 configured to enable removal of disc material positioned at the distal end of a distal extension 51. By way of example, the shaped end 50 comprises a generally round hoop configured to grab and hold disc material for removal, however other shapes and configurations are possible within the scope of the disclosure. The distal extension 51 may be straight or curved.

The distal end 44 further includes one or more sensors 52 in communication with a computer (e.g. stationary desktop and/or laptop) and/or a hand-held computing device (e.g. smart-phone and/or tablet device) used within the medical environment and/or remotely. The communication may be achieved by any method (e.g. via hard wire, WiFi, Bluetooth, "cloud", and the like). The one or more sensors 52 may be configured to (1) establish data points corresponding to the annular borders, and (2) determine the optimal pressure for endplate preparation and/or disc removal. With regard to establishing data points corresponding to annular borders, the proximal end 42 of the manual disc removal instrument 12 may include a button 54 (for example) that when activated by a user signals the computer to capture a location data point. The location data point is determined by the physical location of the sensor 52 relative to an anatomical point of interest (e.g. one or more annular border locations), and the computer uses the information to create a virtual image of the target disc space. Optionally, the computer may cause this virtual image to be displayed on a monitor 18 or other display device in real time (e.g. as an overlay on a fluoroscopic image captured preoperatively) so that a user may receive instant visual confirmation of the data point capture. In the instant example, in which the user intends to create a virtual image of the target disc space, several points of interest of the annular border may be captured, including but not limited to the outer boundary 36 of the annulus at or near the breach 40, the inner boundary 38 of the annulus at or near the breach 40, and the inner boundary 38 of the annulus at one or more points opposite the breach 40. To capture these additional data points, the user positions the distal end 44 near the additional points of interest and presses the button 54. Additional data points may be input manually into the computer by a user from a manual data input device 16, for example on a desktop or laptop station connected to the computer, or a touch-screen interface (e.g. user uses a stylus to draw a boundary or data point on the screen), which is captured by the computer and combined with the sensor-captured data points to finish the virtual image. The computer may also (or alternatively) auto-complete the virtual image by connecting the data points and/or using the preoperative image overlay. Once the virtual image is complete, the computer has the parameters of the annular boundary, and this information may be used in employing a robotic endplate preparation instrument 14 (described below).

In addition to location determination, the one or more sensors 52 of the present example includes a pressure-sensing feature to enable the computer to determine the optimal pressure to employ on the target disc space to remove the disc and prepare endplate during the robotic portion of the method. During manual disc removal and/or endplate preparation, the one or more pressure sensors 52 continuously sense the pressure being applied by the user according to the user's preference (e.g. based on user's experience and "feel"). This data is transmitted (or later uploaded) to the computer, which then provides instructions to the robotic endplate preparation instrument 14 regarding the optimal pressure for endplate preparation.

The manual disc removal instrument 12 of the present example may include additional sensors (or additional functionality associated with sensors 52) that sense and record (or transmit to the computer) data related to the degree of movement of the handle 48 and/or shaft 46. The degree of movement of the handle 48 and/or shaft 46 may be affected by the approach angle and/or the size of the breach 30. This recorded data is processed by the computer and later informs the allowed movement (if any) of the handle/shaft of the robotic endplate preparation instrument 14.

Returning to the method set forth in the flowchart of FIG. 2, the next step 24 is to input the recorded data regarding annular border and preferred endplate preparation pressure into a computer that controls a robotic system configured to perform automated endplate preparation and disc removal. In example described above, this step occurs simultaneously with the previous step as the data collection instrument was described as being in communication with a computer which then processes the data and instructs the automated robotic device using the processed annular border location and pressure data. In some instances the data collection instrument (e.g. manual disc removal instrument 12) may include a data collection and storage feature that is not in direct communication with a computer that processes the data and instructs the robotic instrument 14, and thus a data transfer becomes necessary.

The next step 26 of the method is to position a robotic system such that deployable endplate preparation elements are within the target disc space. One example of an endplate preparation instrument 14 that may be used with a robotic system is illustrated in FIG. 4. By way of example, the robotic endplate preparation instrument 60 of the present example includes a proximal end 62, a distal end 64, and an elongated shaft 66 extending between the proximal end and distal end. The proximal end 62 includes a handle 68, which in turn is attached to a base (not shown). The distal end 64 includes an endplate preparation element 70 (e.g. one or more curettes, blades, whisks, and the like) configured to engage the vertebral endplate and prepare the endplate for receiving fusion material (artificial and/or biologic). The base (not shown) is mounted to a fixed location, for example the patient, a tissue retractor (if used) or the operating table via an articulating arm. According to one example, the base maintains the handle 68 in a fixed position. According to another example, the base may enable slight movement of the handle 68 within a safe boundary of Kambin's Triangle. A data set comprising the safe range of handle movement may be recorded by the computer during the manual disc removal step (e.g. computer recording the degree of manual movement of the handle 48 of the manual disc remover 12) and then translated into movement instructions or parameters for the robotic endplate preparation instrument 60.

Once the robotic system is deployed, the next step 28 is to operate the robotic system to remove disc material and prepare endplates according to recorded data regarding the annular border and preferred endplate preparation pressure. As previously described, the handle 68 is kept in a generally static position (with optional slight movement controlled by the computer) and the endplate preparation element 70 is caused to move independently of the shaft. This movement may include distal extension, proximal retreat, and/or rotational movement. Because the computer "knows" where the annular borders are and also what the optimal pressure to apply to the endplates is by virtue of data collection during the manual disc removal step described above, the computer-operated robotic endplate preparation instrument 14 may prepare the endplates with greater efficiency and precision compared to a manual operator.

The robotic endplate preparation system 10 described herein by way of example only is one example embodiment of using robotics to increase safety and efficiency in techniques that require precision. However robotics may be used throughout the surgical procedure to increase safety and efficiency to several aspects. For example, one such aspect is determining an approach trajectory and establishing an operative corridor to a surgical target site (e.g. an intervertebral disc space). In most cases, this aspect is performed manually by a surgeon who never leaves the X-ray field even though numerous (and in some instances, continuous) radiation exposure events may happen during the procedure. This is especially hazardous for high-volume surgeons. In the current example, one or more surgical needles (e.g. Jamshidi needles) may be attached to the distal end(s) of one or more robotic arms controlled by computer system 4000 (for example). The surgeon can be out of the X-Ray field entirely without giving up the ability to control the positioning of the surgical needle while the medial-lateral approach angle is determined. The robotically-positioned needle(s) may then be verified using additional targeting devices/techniques. Once established, the robotic arm may then continue to hold the surgical needle (and subsequent dilators, retractors, etc.) in place to establish and maintain an operative corridor (e.g. minimally invasive, percutaneous, and/or open).

FIGS. 5-8 illustrate an example of a digital expandable trial instrument 110 having a pressure gauge for use in determining the optimal height expansion of an expandable implant within a given disc space, according to one embodiment of the disclosure. Generally, a distal end of the digital expandable trial instrument 110 is inserted into the prepared disc space and then caused to expand so that it contacts the vertebral endplates. A pressure gauge positioned thereon will be activated upon contact with the vertebral endplates, and will measure and record force data of the expandable trial 110 as it continues to expand and distract the vertebra until a desired stoppage point has been reached. The expandable trial 110 is then returned to a contracted form and removed from the disc space. The information gained through the use of the expandable trial 110 is then used when implanting and expanding an expandable spinal implant 120 (FIG. 1), either manually or robotically.

By way of example, the expandable trial 110 includes an inner shaft, an outer shaft 112, an expandable wedge member 114, and a handle assembly 116. The inner shaft (not shown) comprises an elongated element having proximal and distal ends. The distal end includes an expansion element that interacts with the wedge member 114 to increase the height of the top and bottom faces of the wedge member 114 as the inner shaft is distally advanced. The proximal end includes a lever 118 extending laterally from the handle assembly 116. The lever 116 is operable by a user to manually facilitate advancement of the inner shaft to expand the wedge member 114.

The outer shaft 112 comprises a generally cylindrical hollow tube having a proximal end, a distal end, and an interior lumen extending longitudinally through the outer shaft 112. The interior lumen is sized and configured to receive the inner shaft therein and further enable translation of the inner shaft within the outer shaft 112. The proximal end of the outer shaft is attached to the handle assembly 116.

The wedge member 114 includes first and second expansion panels 120, 122, and first and second pressure sensors 124, 126 associated with the first and second expansion panels 120, 122, respectively. The expansion panels 120, 122 may be forced apart by the inner shaft when the user causes the inner shaft to travel distally along the outer shaft 112.

The handle assembly 116 comprises a housing 128, a display panel 130 positioned on one side of the housing 128, and an attachment member 132 positioned at the proximal end of the housing 128. The lever 118 extends laterally from the housing 128 and is connected to the inner shaft inside the housing 128. The housing 128 may include a longitudinal slot configured to enable translation of the lever 118 and thus expansion of the wedge member 114. The display panel 130 may include a first digital display unit 134 and a second display unit 136. By way of example only, the first display unit 134 may be configured to digitally display a first data set, for example the force applied by the first and second expansion members 120, 122 on the vertebral endplates as communicated by the pressure sensors 124, 126. The second display unit 136 may be configured to display a second data set, for example the amount of expansion of the first and second expansion panels 120, 122 during use.

Thus, digital expandable trial instrument 110 of the present disclosure enables a user to receive real-time information on the pressure exerted by the expandable trial on the vertebral endplates at any given expansion height. The user can then select the appropriate implant for use in the procedure based on the measured pressure and height expansion data.

In some embodiments, the digital expandable trial instrument 110 may be configured to be robotically operable according to instructions communicated to the digital expandable trial instrument 110 by computer system 4000. In some embodiments, the housing 128 further comprises a processor 138 and a communications module 140. In some embodiments, the processor can be configured to receive data from one or more of the sensors (e.g. pressure sensors 124, 126 and/or resistance sensors described below) and programmed to act in response to certain received data (e.g. stop expansion of the trial or implant when resistance sensor indicates alarm). In some embodiments, the processor can be configured to control the operation of the digital expandable trial 110 according to computer code which can be, for example, stored in computer readable media (e.g. memory, etc.) accessible by the processor. In some embodiments, the communications module 140 can be configured to send and/or receive data to and/or from a user device (e.g. computer, smart phone, smart watch, personal digital assistant, tablet computer, etc.). In some embodiments, the user can, via communication with the expandable trial 110 by way of the communications module 140 and/or user input feature affect the operation of the expandable trial 110. The communications module can be configured to communicate via a wired and/or wireless connection with the user device via one or several communications protocols or standards (e.g. Ethernet, Wi-Fi, Bluetooth, etc.).

Figure 8:
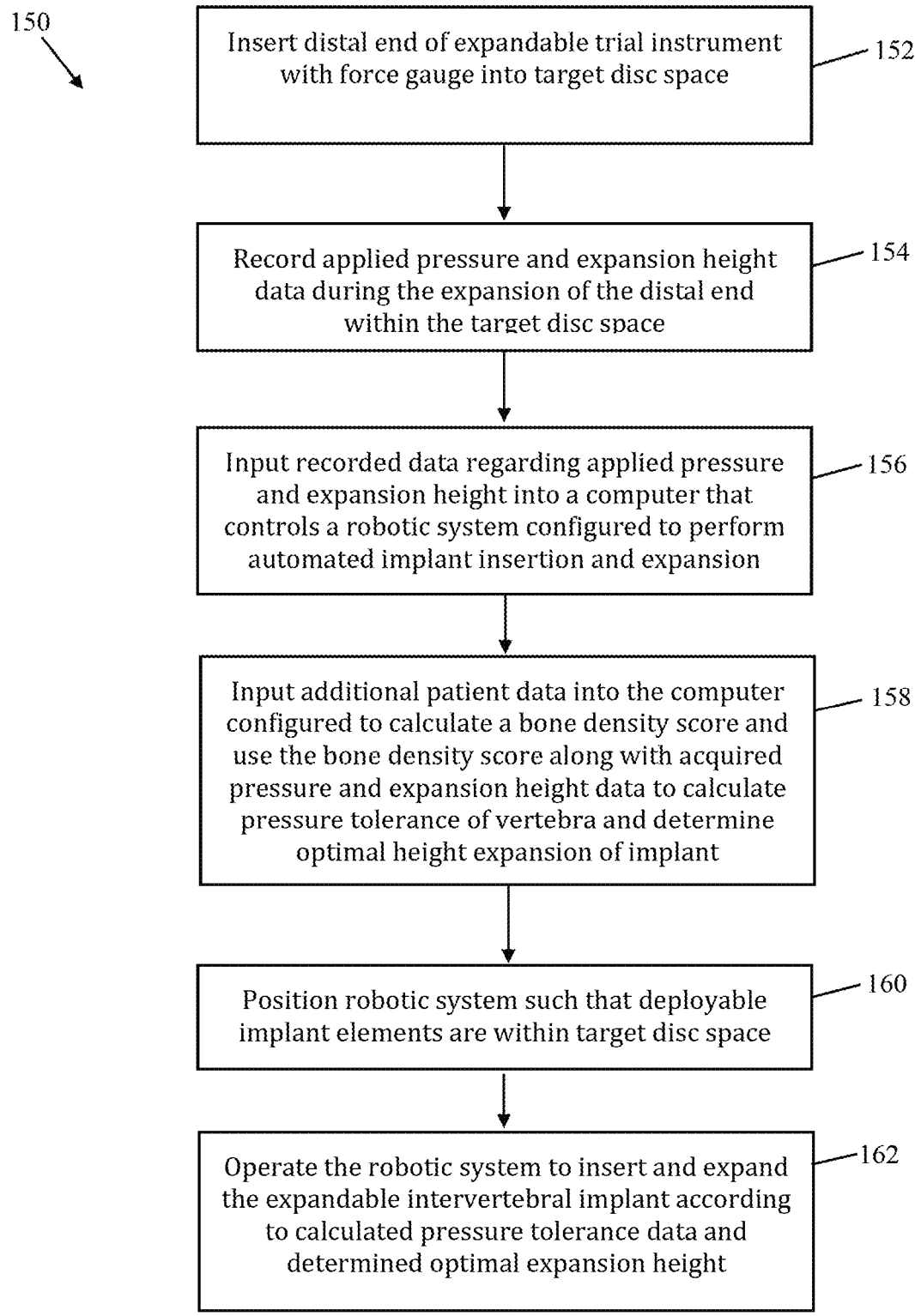
FIG. 8 is a flowchart illustrating one example of a method of performing robotic implant insertion and expansion during a spinal procedure according to one embodiment of the disclosure, according to some embodiments; and, FIG. 9 is a block diagram of computer systems forming part of robotic vertebral endplate preparation system of FIG. 1, according to some embodiments.

FIG. 8 is a flowchart comprising steps of an exemplary method 150 for performing automated insertion and expansion of an expandable implant 210 using the digital expandable trial instrument 110 described herein according to one embodiment of the disclosure. By way of example, the first step 152 is to insert the distal end of the expandable trial instrument 110 with force sensors into the target disc space. The next step 154 is to record applied pressure and expansion height data during the expansion of the distal end of the expandable trial instrument 110. This can occur within a memory unit positioned within the housing 128 of the expandable trial instrument 110 or within computer system 4000. The next step 156 is to input the recorded data regarding applied pressure and expansion height into a computer system 4000 including a processor configured to process the data (if not automatically transferred) and instruct/control a robotic system configured to perform automated implant insertion and expansion.

The next step 158 is to input additional patient data (e.g. age, weight, BMI, etc.) into the computer to calculate a bone density score and use the bone density score along with acquired pressure and expansion height data to calculate the pressure tolerance of the patient's vertebra and determine optimal height expansion of implant. By way of example, the pressure tolerance may be presented to the user as a range or "safe zone" including a color-coded visual indicator (e.g. green for "safe", yellows for "caution", red for "stop").

The next step 160 is to position a robotic implant delivery system such that deployable implant elements are within the target disc space. Finally the last step 162 is to operate the robotic implant delivery system to insert and expand the expandable intervertebral implant according to calculated pressure tolerance data and determined optimal expansion height.

One of skill should appreciate that a functioning and safe robotic system can be created, using the systems and methods herein, to apply a range of acceptable pressures to an animal tissue through a functional portion of a surgical instrument. In some embodiments, the range of acceptable pressures applied can also apply to the implantation of a device, for example.

Such systems can include, for example, a surgical instrument having a functional portion, a robotic arm configured for holding the surgical instrument and contacting the functional portion of the surgical instrument with an animal tissue using a pressure from within a range of acceptable pressures, a pressure application component operably coupled to the robot arm to apply the pressure from within the range of acceptable pressures when contacting the functional portion with the animal tissue.

A computer can be operably attached to the systems and methods provided herein, in which the computer can have a processor; and, a memory, wherein the memory can be configured to include, for example, a governing module on a non-transitory computer readable storage medium. The governing module can be configured such that it is operable to instruct the processor to limit any pressure applied by the robotic arm. For example, the pressure can be limited on the functional portion of the surgical instrument, or implant device, to fall within the range of acceptable pressures when contacting the functional portion with the animal tissue.

It is important to note that even though the various method steps disclosed herein are driven by robotics, they are not necessarily occurring unsupervised, but rather trained surgeons and/or technicians are nearby monitoring the data collection and operation of the robotics instrument. In the event that anything appears to be out of line for them, they have the ability to halt the procedure (e.g. by pressing a "STOP" button or other user input to instruct the computer to stop or change course). One advantage of using robotics to control the precision movements of the procedure is that the surgeons and/or technicians can be out of the X-Ray field and still have the ability to monitor and/or control the action of the robotics.

During spine procedures, one or more of the instruments and/or implants may penetrate (or "sink" into) the bone surface of the vertebral endplate. Too much penetration can be problematic with regard to maintaining the integrity of the bone as well as affecting the efficacy of the procedure (e.g. too much sink may render the implant ineffective). Thus in some embodiments, any one or all of the devices disclosed herein by way of example only (e.g. manual disc removal tool 12, expandable trial 110, intervertebral implant 210, etc.) may include one or more resistance sensors (or "stress sensors") strategically positioned on vertebral contact surfaces to measure penetration into bone and alert the user if the device has over-penetrated the bone. By way of example, the resistance sensors may be placed at certain vertical intervals (e.g. 0.5 mm intervals displaced vertically relative to the vertebral contact surface). The various devices (or coupled inserter, in the case of an implant) may be electrified (e.g. produce or conduct an electric current therethrough) and also include or be connected to a component to measure resistance (e.g. ohmmeter). The electric current is applied and resistance measured in a continuous fashion as the device is in contact with bone. A drop in resistance signifies that device penetrated the bone at a level in which the resistance sensor comes into contact with bone. In some embodiments, this may also trigger an alert or indicator to inform the user that the device has penetrated bone to a certain level. The alert or indicator may be a visual indicator (e.g. illuminated light) and/or audio indicator (e.g. alarm). In some embodiments, the device may include a plurality of visual and/or audio indicators to differentiate between depths of penetration (e.g. more urgent alarm for deeper penetration).

In some embodiments, the robotics may be provided in a modular configuration, in that only the components needed for a particular procedure are brought into the surgical space. In some embodiments, one or more of the component may have additional sensors to detect and record various data, for example the total radiation exposure.

Figure 9:
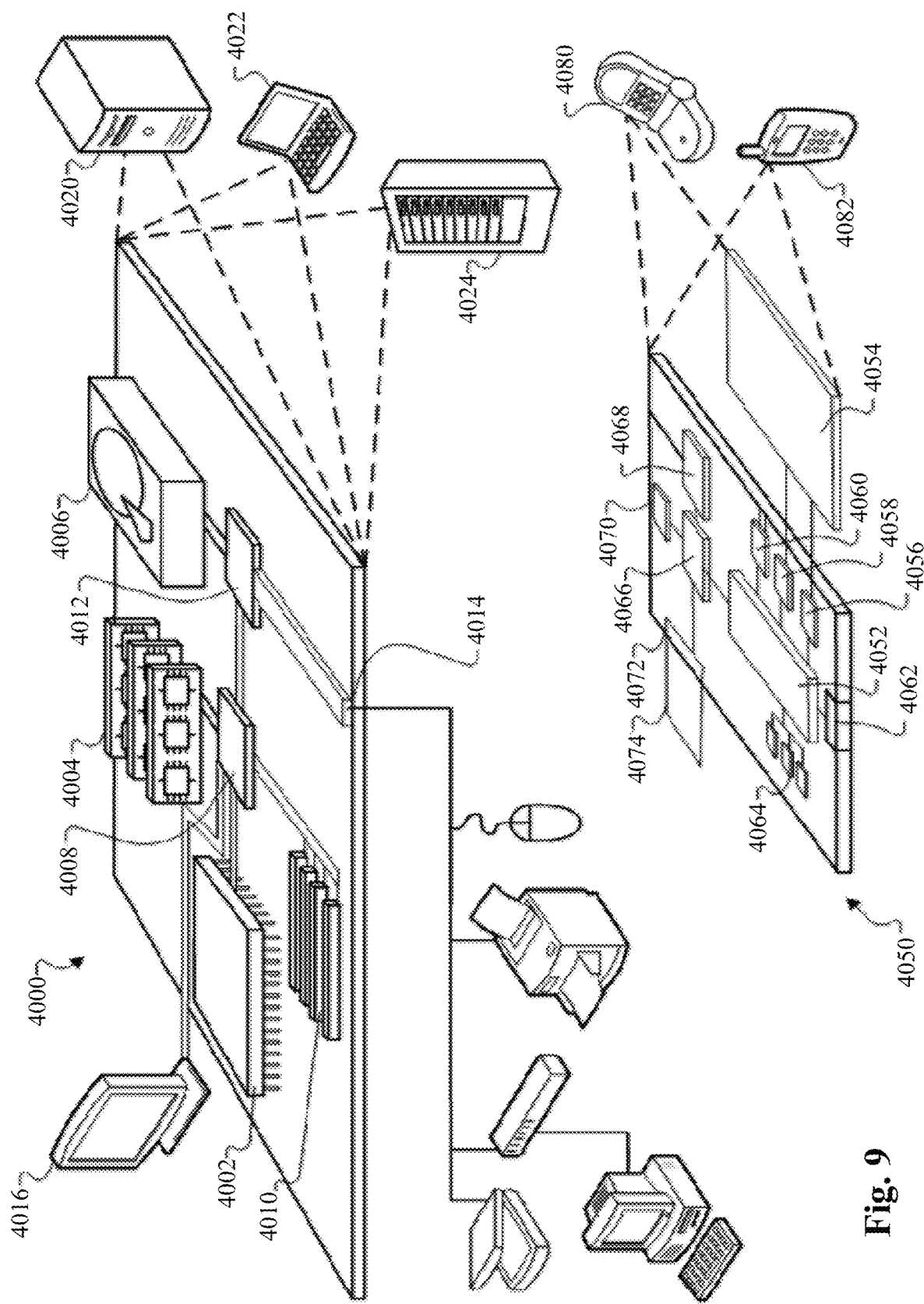

FIG. 9 is a block diagram of computing devices 4000, 4050 that may be used to implement the systems and methods described in this document, as either a client or as a server or plurality of servers. Computing device 4000 is intended to represent various forms of digital computers, such as laptops, desktops, workstations, personal digital assistants, servers, blade servers, mainframes, and other appropriate computers. Computing device 4050 is intended to represent various forms of mobile devices, such as personal digital assistants, cellular telephones, smartphones, and other similar computing devices. In this example, computing device 4050 may represent a handheld device, while computing device 4000 may represent one or ore stationary computing systems including a terminal within the medical environment and/or one or more servers that serve as the "cloud" referenced in this disclosure. The components shown here, their connections and relationships, and their functions, are meant to be examples only, and are not meant to limit implementations described and/or claimed in this document.

Computing device 4000 includes a processor 4002, memory 4004, a storage device 4006, a high-speed interface 4008 connecting to memory 4004 and high-speed expansion ports 4010, and a low speed interface 4012 connecting to low speed bus 4014 and storage device 4006. Each of the components 4002, 4004, 4006, 4008, 4010, and 4012, are interconnected using various busses, and may be mounted on a common motherboard or in other manners as appropriate. The processor 4002 can process instructions for execution within the computing device 4000, including instructions stored in the memory 4004 or on the storage device 4006 to display graphical information for a GUI on an external input/output device, such as display 4016 coupled to high-speed interface 4008. In other implementations, multiple processors and/or multiple buses may be used, as appropriate, along with multiple memories and types of memory. Also, multiple computing devices 4000 may be connected, with each device providing portions of the necessary operations (e.g., as a server bank, a group of blade servers, or a multi-processor system).

The memory 4004 stores information within the computing device 4000. In one implementation, the memory 4004 is a volatile memory unit or units. In another implementation, the memory 4004 is a non-volatile memory unit or units. The memory 4004 may also be another form of computer-readable medium, such as a magnetic or optical disk.

The storage device 4006 is capable of providing mass storage for the computing device 4000. In one implementation, the storage device 4006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 4004, the storage device 4006, or memory on processor 4002.

The high-speed controller 4008 manages bandwidth-intensive operations for the computing device 4000, while the low speed controller 4012 manages lower bandwidth-intensive operations. Such allocation of functions is by way of example only. In one implementation, the high-speed controller 4008 is coupled to memory 4004, display 4016 (e.g., through a graphics processor or accelerator), and to high-speed expansion ports 4010, which may accept various expansion cards (not shown). In the implementation, low-speed controller 4012 is coupled to storage device 4006 and low-speed expansion port 4014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 4000 may be implemented in a number of different forms, as shown in the figure. For example, it may be implemented as a standard server 4020, or multiple times in a group of such servers. It may also be implemented as part of a rack server system 4024. In addition, it may be implemented in a personal computer such as a laptop computer 4022. Alternatively, components from computing device 4000 may be combined with other components in a mobile device (not shown), such as device 4050. Each of such devices may contain one or more of computing device 4000, 4050, and an entire system may be made up of multiple computing devices 4000, 4050 communicating with each other.

Computing device 4050 includes a processor 4052, memory 4064, an input/output device such as a display 4054, a communication interface 4066, and a transceiver 4068, among other components. The device 4050 may also be provided with a storage device, such as a microdrive or other device, to provide additional storage. Each of the components 4050, 4052, 4064, 4054, 4066, and 4068, are interconnected using various buses, and several of the components may be mounted on a common motherboard or in other manners as appropriate.

The processor 4052 can execute instructions within the computing device 4050, including instructions stored in the memory 4064. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 4050, such as control of user interfaces, applications run by device 4050, and wireless communication by device 4050.

Processor 4052 may communicate with a user through control interface 4058 and display interface 4056 coupled to a display 4054. The display 4054 may be, for example, a TFT (Thin-Film-Transistor Liquid Crystal Display) display or an OLED (Organic Light Emitting Diode) display, or other appropriate display technology. The display interface 4056 may comprise appropriate circuitry for driving the display 4054 to present graphical and other information to a user. The control interface 4058 may receive commands from a user and convert them for submission to the processor 4052. In addition, an external interface 4062 may be provided in communication with processor 4052, so as to enable near area communication of device 4050 with other devices. External interface 4062 may provide, for example, for wired communication in some implementations, or for wireless communication in other implementations, and multiple interfaces may also be used.

The memory 4064 stores information within the computing device 4050. The memory 4064 can be implemented as one or more of a computer-readable medium or media, a volatile memory unit or units, or a non-volatile memory unit or units. Expansion memory 4074 may also be provided and connected to device 4050 through expansion interface 4072, which may include, for example, a SIMM (Single In Line Memory Module) card interface. Such expansion memory 4074 may provide extra storage space for device 4050, or may also store applications or other information for device 4050. Specifically, expansion memory 4074 may include instructions to carry out or supplement the processes described above, and may include secure information also. Thus, for example, expansion memory 4074 may be provided as a security module for device 4050, and may be programmed with instructions that permit secure use of device 4050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, cause performance of one or more methods, such as those described above. The information carrier is a computer- or machine-readable medium, such as the memory 4064, expansion memory 4074, or memory on processor 4052 that may be received, for example, over transceiver 4068 or external interface 4062.

Device 4050 may communicate wirelessly through communication interface 4066, which may include digital signal processing circuitry where necessary. Communication interface 4066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 4068. In addition, short-range communication may occur, such as using a Bluetooth, WiFi, or other such transceiver (not shown). In addition, GPS (Global Positioning System) receiver module 4070 may provide additional navigation- and location-related wireless data to device 4050, which may be used as appropriate by applications running on device 4050.

Device 4050 may also communicate audibly using audio codec 4060, which may receive spoken information from a user and convert it to usable digital information. Audio codec 4060 may likewise generate audible sound for a user, such as through a speaker, e.g., in a handset of device 4050. Such sound may include sound from voice telephone calls, may include recorded sound (e.g., voice messages, music files, etc.) and may also include sound generated by applications operating on device 4050.

The computing device 4050 may be implemented in a number of different forms, some of which are shown in the figure. For example, it may be implemented as a cellular telephone 4080. It may also be implemented as part of a smartphone 4082, personal digital assistant, or other similar mobile device.

Additionally computing device 4000 or 4050 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the invention.

I claim:

1. A robotic surgical system for identifying a surgical region in which to apply an acceptable range of pressures to a functional portion of a surgical instrument against an animal tissue, the system comprising:
   a surgical instrument having a functional portion that contacts an animal tissue having a defined surgical region through application of pressure by an operator of the surgical instrument;
   a robotic arm configured for holding the surgical instrument and contacting the functional portion of the surgical instrument with the animal tissue using a pressure from within a range of acceptable pressures;
   a pressure application component operably coupled to the robot arm to apply the pressure from within the range of acceptable pressures when contacting the functional portion with the animal tissue;
   a pressure sensor in an operable association with the functional portion operable to measure the pressure applied by the operator to the functional portion in contact with the animal tissue;
   a computer having a processor; and, a memory including
      a pressure module on a non-transitory computer readable storage medium operable to create pressure data representing the pressure applied by the operator to the functional portion in contact with the animal tissue;
      a design module on a non-transitory computer readable storage medium operable for establishing a pressure profile output that identifies the range of acceptable pressures for use in contacting a type of animal tissue, the animal tissue in contact with the functional portion;
      a governing module on a non-transitory computer readable storage medium, wherein the governing module is operable to limit the pressure applied by the robotic arm on the functional portion to the range of acceptable pressures when contacting the functional portion with the animal tissue; wherein the range of acceptable pressures is selected by a process that includes
         analyzing pressure data representing a total range of pressures on a computer having a processor and a memory having a pressure module on a non-transitory computer readable storage medium and a database on a non-transitory computer readable storage medium, the analyzing including
            creating the pressure data with the pressure module, the pressure data representing the pressure applied by the operator to the functional portion in contact with the animal tissue; and,
            selecting the range of acceptable of pressures;
   and,
   a database on a non-transitory computer readable storage medium operable to store the pressure data;
   wherein, the robotic surgical system gathers data to (i) locate tissue borders of the surgical site, (ii) identify a preferred pressure, and (iii) transmit the data to the computer to avoid violating the integrity of the tissue borders surrounding the surgical site.

2. The system of claim 1, further comprising an input module on a non-transitory computer readable storage medium for receiving operator input identifying
   the type of animal tissue receiving the pressure applied by the operator;
   a type of function obtained by the functional portion on the animal tissue receiving the pressure applied by the operator;
   a type of result, including a positive result and/or a negative result, of the pressure applied to the functional portion on the animal tissue receiving the pressure applied by the operator; or,
   a combination thereof.

3. The system of claim 2, wherein the design module is used to obtain the type of function, and the positive results, when contacting the functional portion with the animal tissue.

4. The system of claim 1, wherein the surgical instrument is a cutting instrument or a dissecting instrument.

5. The system of claim 1, wherein the surgical instrument is a grasping instrument or a holding instrument.

6. The system of claim 1, wherein the surgical instrument is a hemostatic instrument.

7. The system of claim 1, wherein the surgical instrument is a retraction instrument.

8. The system of claim 1, wherein the surgical instrument is a tissue-unifying instrument.

9. The system of claim 1, wherein the functional portion of the surgical instrument is configured to remove nucleus pulposus tissue.

10. The system of claim 1, wherein the operator is a human.

11. The system of claim 1, wherein the operator is a mechanical device.

12. A method of (i) locating tissue borders of a surgical site, (ii) identifying a preferred pressure, and (iii) transmitting data to a computer to avoid violating the integrity of tissue surrounding the surgical site, the method comprising:
obtaining the robotic surgical system of claim 1;
obtaining the surgical instrument having
one or more sensors to gather data related to the location of the tissue borders and/or the preferred pressure, the sensors in communication with the computer;
contacting the functional portion of the surgical instrument with the tissue of the animal with a total range of pressures; and,
analyzing the pressure data representing the total range of pressures on a computer having a processor and a memory having a pressure module on a non-transitory computer readable storage medium and a database on a non-transitory computer readable storage medium, the analyzing including
creating the pressure data with the pressure module, the pressure data representing the pressure applied by the operator to the functional portion in contact with the animal tissue; and,
storing the pressure data on the database;
selecting the range of acceptable pressures for use in contacting the functional portion with the animal tissue; and,
transmitting the data gathered on the location of the tissue borders to avoid violating the integrity of the tissue surrounding the surgical site.

13. The method of claim 12, further comprising correlating operator input with results obtained from contacting the functional portion with the animal tissue, the correlating including,
receiving the operator input with an input module on a non-transitory computer readable storage medium; and, identifying
the type of animal tissue receiving the pressure applied by the operator;
a type of function obtained by the functional portion on the animal tissue receiving the pressure applied by the operator;
a type of result, including a positive result and/or a negative result, of the pressure applied through the functional portion on the animal tissue; or,
a combination thereof;
and,
using the data gathered and transmitted to the computer to create a virtual image of a target disc space.

14. The method of claim 13, wherein the animal tissue is a vertebral disc, the border is an annular border, and the method further comprises
designing a pressure profile using the design module on the non-transitory computer readable storage medium operable for establishing the pressure profile output that identifies the range of acceptable pressures for use in contacting the type of animal tissue, to obtain the type of function, and the positive results, when contacting the functional portion with the animal tissue.

15. A robotic system calibrated to identify borders and to apply a range of acceptable pressures to a vertebral disc through a functional portion of a surgical instrument, the system comprising:
a surgical instrument having a functional portion;
a robotic arm configured for holding the surgical instrument and contacting the functional portion of the surgical instrument with an animal tissue using a pressure from within a range of acceptable pressures;
a pressure application component operably coupled to the robotic arm to apply the pressure from within the range of acceptable pressures when contacting the functional portion with the animal tissue;
a processor; and,
a memory including
a governing module on a non-transitory computer readable storage medium, wherein the governing module is operable to limit the pressure applied by the robotic arm on the functional portion to the range of acceptable pressures when contacting the functional portion with the animal tissue; wherein the range of acceptable pressures is selected by a process that includes
analyzing pressure data representing a total range of pressures on a computer having a processor and a memory having a pressure module on a non-transitory computer readable storage medium and a database on a non-transitory computer readable storage medium, the analyzing including
creating the pressure data with the pressure module, the pressure data representing a pressure applied by an operator to the functional portion in contact with the animal tissue; and,
selecting the range of acceptable of pressures;
wherein, the robotic surgical system gathers data to (i) locate the borders of an annulus of the vertebral disc, (ii) identify a preferred pressure, and (iii) transmit the data to the computer to avoid violating the integrity of the animal tissue surrounding the vertebral disc.

16. The system of claim 15, wherein the surgical instrument is a cutting instrument or a dissecting instrument.

17. The system of claim 15, wherein the surgical instrument is selected from the group consisting of a grasping instrument or a holding instrument, a hemostatic instrument, a retraction instrument, and a tissue-unifying instrument.

18. The system of claim 15, wherein the animal tissue includes intervertebral tissue and cortical portion of a vertebral endplate, the functional portion of the surgical instrument is configured to remove the intervertebral tissue, and the acceptable range of pressures is designed to remove the intervertebral tissue without violating the cortical portion of the vertebral endplate.

19. A method of using the system of claim 15 to prepare an intervertebral disc for a spinal fusion procedure, the method comprising
creating a point of entry into an intervertebral disc, the intervertebral disc having a nucleus pulposus surrounded by an annulus fibrosis;
obtaining the surgical instrument having
the functional portion configured for contacting the intervertebral disc with the pressure applied by the operator of the surgical instrument, the functional portion of the surgical instrument being in an operable association with a pressure sensor for measuring the pressure applied by the operator to the functional portion in contact with the intervertebral disc
one or more sensors to gather data related to a location of the borders and/or the preferred pressure, the sensors in communication with the computer;
using the one or more sensors to gather data related to the location of the borders of the intervertebral disc and/or the preferred pressure, the sensors in communication with the computer;
and,
removing intervertebral tissue from within an intervertebral space, the intervertebral space having a top vertebral plate and a bottom vertebral plate while preserving the annulus fibrosis and without violating the integrity of a cortical portion of (i) the top vertebral plate or (ii) the bottom vertebral plate, wherein the removing includes limiting the pressure applied by the robotic arm on the functional portion of the surgical instrument to the intervertebral tissue to a pressure from within the range of acceptable pressures.

20. The method of claim 19, further comprising:

inserting a scaffolding through the point of entry into the intervertebral disc;

and, adding a grafting material to the intervertebral space.

* * * * *